(12) United States Patent
Beswick et al.

(10) Patent No.: US 7,196,107 B2
(45) Date of Patent: Mar. 27, 2007

(54) THIA-AND OXAZOLES AND THEIR USE AS PPARS ACTIVATORS

(75) Inventors: Paul John Beswick, Stevenage (GB); Vipulkumar Patel, Stevenage (GB); Michael Lawrence Sierra, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 421 days.

(21) Appl. No.: 10/451,307

(22) PCT Filed: Dec. 18, 2001

(86) PCT No.: PCT/EP01/14887

§ 371 (c)(1), (2), (4) Date: Nov. 17, 2003

(87) PCT Pub. No.: WO02/50048

PCT Pub. Date: Jun. 27, 2002

(65) Prior Publication Data

US 2004/0102493 A1 May 27, 2004

(30) Foreign Application Priority Data

Dec. 20, 2002 (GB) .................................. 0031109.2

(51) Int. Cl.
- A61K 31/426 (2006.01)
- A61K 31/421 (2006.01)
- C07D 277/20 (2006.01)
- C07D 263/30 (2006.01)

(52) U.S. Cl. .................. 514/365; 548/203; 548/204; 548/235; 548/236; 514/374

(58) Field of Classification Search ............... 548/146, 548/202, 203, 204, 235, 236; 514/365, 374
See application file for complete search history.

(56) References Cited

U.S. PATENT DOCUMENTS

| | | | |
|---|---|---|---|
| 6,518,290 B1 * | 2/2003 | Sierra .................. | 514/365 |
| 6,710,063 B1 * | 3/2004 | Chao et al. ............ | 514/365 |
| 6,723,740 B2 * | 4/2004 | Chao et al. ............ | 514/365 |

FOREIGN PATENT DOCUMENTS

| EP | 0 930 299 | 7/1999 |
|---|---|---|
| WO | 01/00603 | 1/2001 |
| WO | 01/16120 | 3/2001 |
| WO | 02/14291 | 2/2002 |
| WO | 02/059098 | 8/2002 |
| WO | 02/062774 | 8/2002 |

OTHER PUBLICATIONS

Shinkai, H. et al., "Isoxazolindine-3,5-dione and noncyclic 1,3-dicarbonyl compounds as hypoglycemic agents," *Journal of Medicinal Chemistry*, vol. 41, No. 11, pp. 1927-1933, May 21, 1998.

Bright, S.W., et al., "Competitive Particle Concentration Fluorescence Immunoassays for Measuring Anti-diabetic Drug Levels in Mouse Plasma," *Journal of Immunological Methods*, vol. 207, No. 1, pp. 23-31, Aug. 22, 1997.

* cited by examiner

Primary Examiner—Golam M. M. Shameem
(74) Attorney, Agent, or Firm—Jennifer L. Fox

(57) ABSTRACT

A compound of formula (I) or pharmaceutically acceptable salts and solvates thereof. $R^1$ and $R_2$ are independently H or $C_{1-3}$alkyl, m is 0–3; $X^1$ is NH, $NCH_3$, O, S; $R^3$, $R^4$ and $R^5$ are independently H, $CH_3$, $CF_3$, $OCH_3$, allyl or halogen; $X^2$ is $(CR^{10}R^{11})n$ wherein n is 1 or 2; $R^{10}$ and $R^{11}$ independently represent H, fluorine or $C_{1-16}$alkyl; $R^{26}$ and $R^{27}$ are independently H, $C_{1-3}$ alkyl or $R^{26}$ and $R^{27}$ together with the carbon atom to which they are bonded form a 3–5 membered cycloalklyl ring. $R^6$ and $R^7$ independently represent H, fluorine or $C_{1-16}$alkyl; $R^9$ is $C_{1-6}$alkyl or $CF_3$; One of Y and Z is N, the other is S or O; Each $R^8$ independently represents $CF_3$, $OCH_3$, $CH_3$ or halogen; y is 0, 1, 2, 3, 4, 5. Use of a compound of formula (I) for the manufacture of a medicament for the prevention or treatment of a hPPAR mediated disease or condition, such as dyslipidemia, syndrome X, heart failure, hypercholesteremia, cardiovascular disease, type II diabetes mellitus, type 1 diabetes, insulin resistance hyperlipidemia, obesity, anorexia bulimia, inflammation and anorexia nervosa

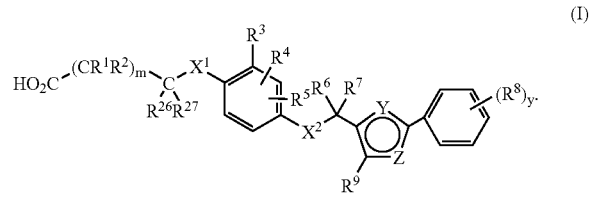

3 Claims, No Drawings

THIA-AND OXAZOLES AND THEIR USE AS PPARS ACTIVATORS

This application is filed pursuant to 35 U.S.C. § 371 as a United States National Phase Application of International Application No. PCT/EPO1/14887 filed Dec. 18, 2001, which claims priority from 0031109.2 filed Dec. 20, 2000.

The present invention relates to certain novel compounds. In particular, the present invention relates to compounds that activate human peroxisome proliferator activated receptors ("hPPARs") particularly hPPAR subtype delta. The present invention also relates to methods for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. Curr. Pharm. Des. 1998, 4, 53–70).

Syndrome X (including metabolic syndrome) is loosely defined as a collection of abnormalities including hyperinsulemia, obesity, elevated levels of trigycerides, uric acid, fibrinogen, small dense LDL particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., Curr. Opin. Chem. Biol. (1997) Vol 1 pp 235–241 and Willson T. M. et. al., J. Med. Chem (2000) Vol 43 p 527–549. The binding of agonist ligands to the receptor results in changes in the expression level of MRNA's enclded by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, Trends Endocrin. Met 291–296, 4 (1993)).

It has now been reported that thiazolidinediones are potent and selective activators of PPAR-gamma and bind directly to the PPAR-gamma receptor (J. M. Lehmann et. al., J. Biol. Chem. 12953–12956, 270 (1995)), providing evidence that PPAR-gamma is a possible target for the therapeutic actions of the thiazolidinediones.

Activators of the nuclear receptor PPARγ, for example troglitazone, have been shown in the clinic to enhance insulin-action, reduce serum glucose and have small but significant effects on reducing serum triglyceride levels in patients with Type 2 diabetes. See, for example, D. E. Kelly et al., Curr. Opin. Endocrinol. Diabetes, 90–96, 5 (2), (1998); M. D. Johnson et al., Ann. Pharmacother., 337–348, 32 (3), (1997); and M. Leutenegger et al., Curr. Ther. Res., 403–416, 58 (7), (1997).

The mechanism for this triglyceride lowering effect appears to be predominantly increased clearance of very low density lipoproteins (VLDL) through induction of liporotein lipase (LPL) gene expression. See, for example, B. Staels et al., Arterioscler. Thromb., Vasc. Biol., 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., Curr. Pharm. Des., 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., Atherosclerosis, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.). In a recent report (Berger et al., J. Biol. Chem. 1999), vol. 274, pp. 6718–6725) it was stated that PPARδ activation does not appear to modulate glucose or triglyceride levels.

Accordingly, the present invention provides a compound of formula (I) and pharmaceutically acceptable salts, hydrolysable esters and solvates thereof;

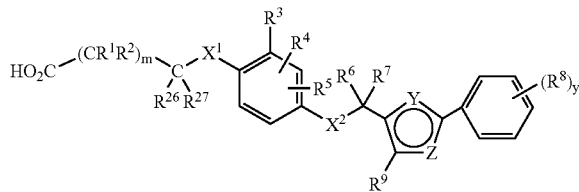

(IC)

$R^1$ and $R^2$ are independently H or $C_{1-3}$alkyl m is 0–3;

$X^1$ is NH, $NCH_3$, O, S;

$R^3$, $R^4$ and $R^5$ are independently H, $CH_3$, $CF_3$, $OCH_3$, allyl or halogen;

$X^2$ is $(CR^{10}R^{11})n$ wherein n is 1 or 2;

$R^{10}$ and $R^{11}$ independently represent H, fluorine or $C_{1-6}$ alkyl;

$R^{26}$ and $R^{27}$ are independently H, $C_{1-3}$ alkyl or $R^{26}$ and $R^{27}$ together with the carbon atom to which they are bonded form a 3–5 membered cycloalkyl ring.

$R^6$ and $R^7$ independently represent H, fluorine or $C_{1-6}$ alkyl;

$R^9$ is $C_{1-6}$ alkyl or $CF_3$;

One of Y and Z is N, the other is S or O;

Each $R^8$ independently represents $CF_3$, $OCH_3$, $CH_3$ or halogen;

y is 0, 1, 2, 3, 4, 5.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable hydrolysable ester or, solvate, thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably m is 0, 1 or 3, more preferably 0;

Preferably $X^1$ is NH or O, more preferably O.

$R^3$ is preferably $CH_3$ or $CF_3$;

$R^{10}$ and $R^{11}$ preferably independently represent H or F, more preferably H.

$R^6$ and $R^7$ are preferably independently H, F or $CH_3$.

Preferably y is 1 or 2. When y is 2, preferably one of the substituents is halogen; more preferably one is halogen and the other is $CF_3$. More preferably y is 1. When y is 1, preferably the substituent is in the para position on the ring and is more preferably $CF_3$.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferably, the compounds of formula (I) are hPPAR agonists. The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARδ, in the binding assay described below, and which achieve at least 50% activation of the relevant PPAR relative to the appropriate indicated positive control in the transfection assay described below at concentrations of $10^{-5}$ M or less. More preferably, the compounds of this invention achieve 50% activation of at least one human PPAR in the relevant transfection assay at concentrations of $10^{-6}$ M or less. More preferably the compounds of the invention achieve 50% activation of at least one human PPAR in the relevant transfection assay at concentrations of $10^{-7}$ M or less.

Preferred compounds of formula 1 include sodium [4-[({4-methyl-2-[4-(trifluoromethyl)phenyl]-1,3-thiazol-5-yl}methyl)thio]-2-(trifluoromethyl)phenoxy]acetate 4-({2-methyl-4-[({4-methyl-2-[4-(trifluoromethyl)phenyl]-1,3-thiazol-5-yl}methyl)thio]phenyl}amino)butanoic acid 3-({2-methyl-4-[({4-methyl-2-[4-(trifluoromethyl)phenyl]-1,3-thiazol-5-yl}methyl)thio]phenyl}amino)propanoic acid 5-[2-methyl-4-(2-{4-methyl-2-[4-(trifluoromethyl)phenyl]-1,3-thiazol-5-yl}ethyl)phenoxy]pentanoic acid 4-[2-methyl-4-(2-{4-methyl-2-[4-(trifluoromethyl)phenyl]-1,3-thiazol-5-yl}ethyl)phenoxy]butanoic acid

[2-methyl-4-(2-{4-methyl-2-[4-(trifluoromethyl)phenyl]-1,3-thiazol-5-yl}ethyl)phenoxy]acetic acid

[4-(1,1-difluoro-3-{4-methyl-2-[4-(trifluoromethyl)phenyl]-1,3-thiazol-5-yl}propyl)-2-methylphenoxy]acetic acid

[4-(1-fluoro-2-{4-methyl-2-[4-(trifluoromethyl)phenyl]-1,3-thiazol-5-yl}ethyl)-2-methylphenoxy]acetic acid

[2-methyl-4-(1,1,2-trifluoro-2-{4-methyl-2-[4-(trifluoromethyl)phenyl]-1,3-thiazol-5-yl}ethyl)phenoxy]acetic acid

[2-methyl-4-(1,1,2,2-tetrafluoro-2-{4-methyl-2-[4-(trifluoromethyl)phenyl]-1,3-thiazol-5-yl}ethyl)phenoxy]acetic acid

[2-methyl-4-(3-{4-methyl-2-[4-(trifluoromethyl)phenyl]-1,3-thiazol-5-yl}propyl)phenoxy]acetic acid Preferred compounds are agonists of hPPAR delta.

Compounds of formula 1 may conveniently be prepared by routes shown in the schemes below:

Scheme 1

By alkylation of an intermediate A with a haloalkanoic ester. Intermediate A (e.g. where Y=S and Z=N) can be prepared, by the route outlined below.

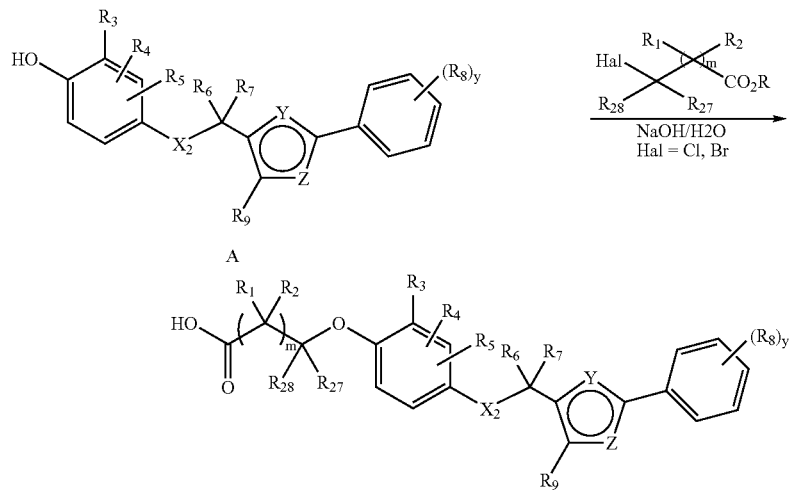

Intermediate A (Y=S, Z=N) may be prepared as follows:

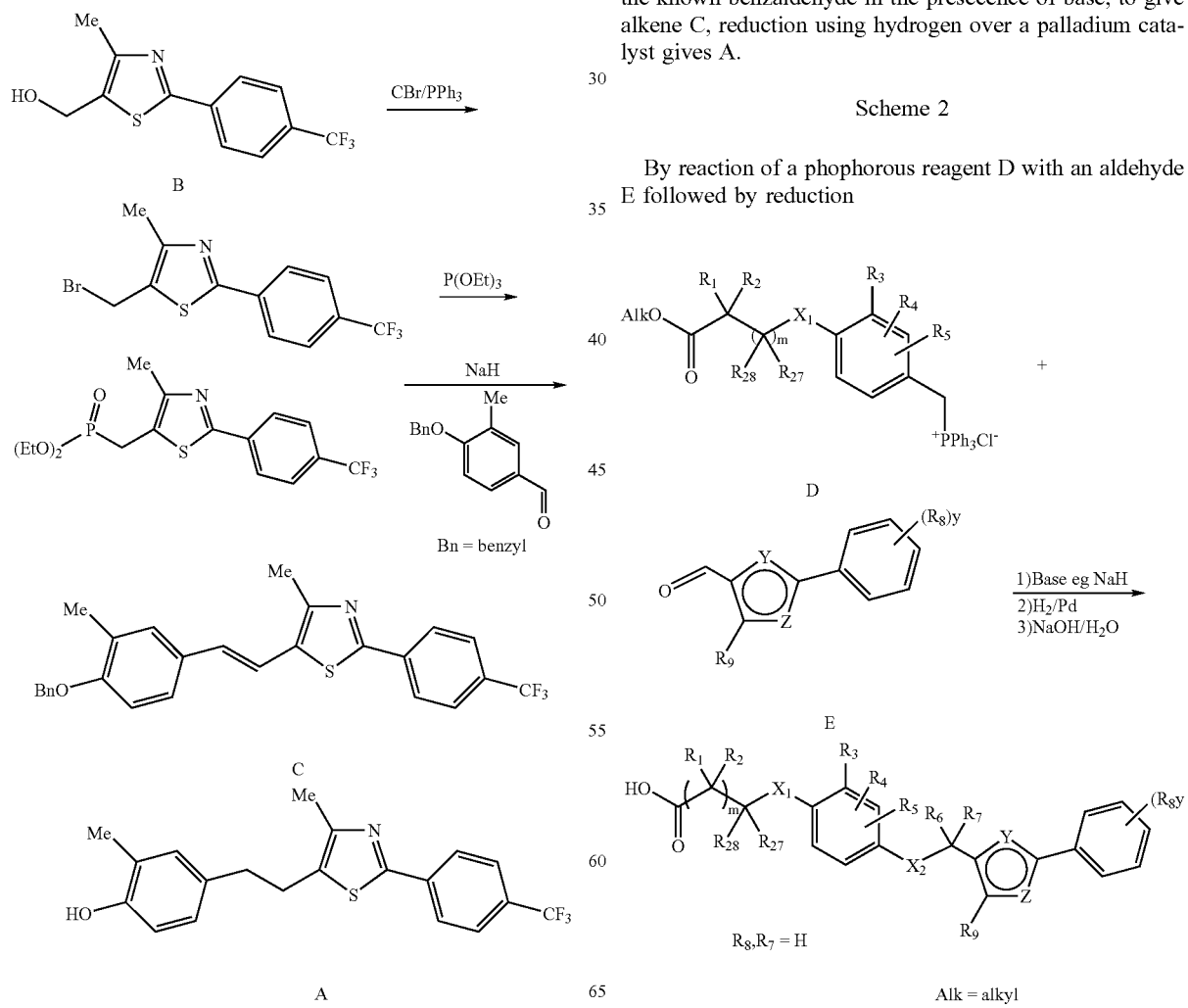

The thiazole alcohol B, prepared from the commercially available ester, is converted to the bromide and then to the phophonate (Org. React., 1951, 6, 273), which reacts with the known benzaldehyde in the presecence of base, to give alkene C, reduction using hydrogen over a palladium catalyst gives A.

Scheme 2

By reaction of a phophorous reagent D with an aldehyde E followed by reduction

Phosphorous reagent D can be prepared from a compound such as a commercially available ester F by treatment with formaldehyde and hydrochloric acid (Org. React. 1942, 1, 303) to give chloride G followed by reaction with triphenylphosphine Scheme 3

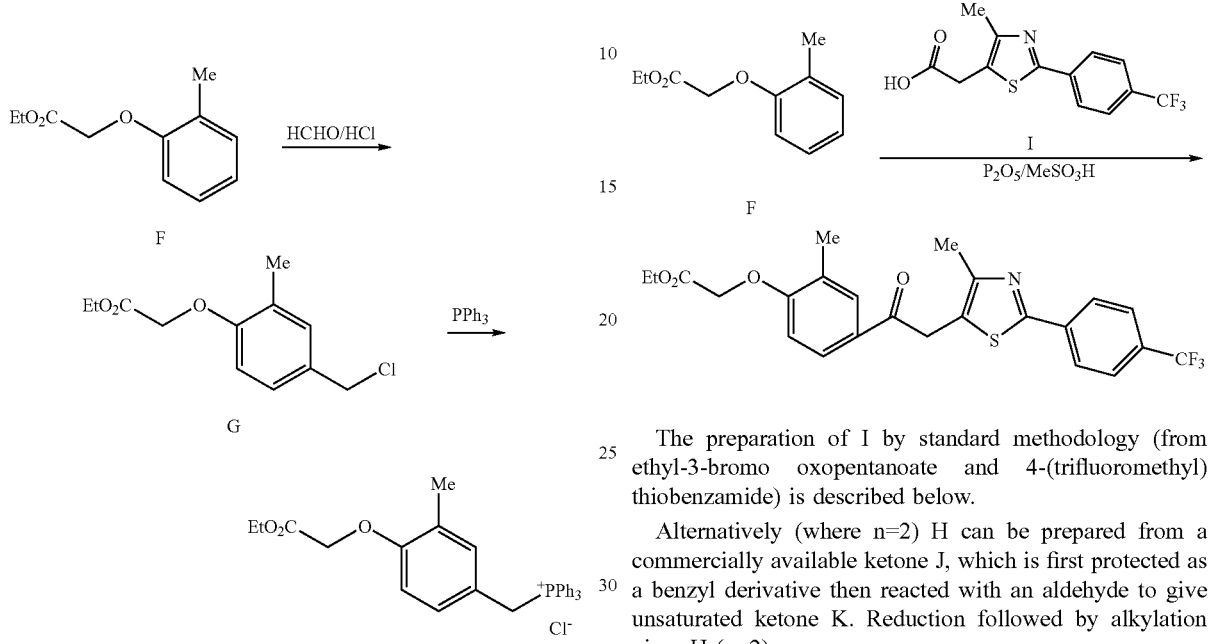

By fluorination of a ketone or alcohol (prepared by reducing ketone H by standard methods eg sodium borohydride), using a reagent such as Deoxyfluor® [bis(2-methoxyethyl)aminosulphurtrifluoride—J. Org. Chem., 1999, 64, 7048–7054]. In the case where n=1 fluorination is also observed on the neighbouring carbon atom (ie $R_6$ and/or $R_7$ can be fluorine in addition to $X_2$ being CF2.

Alternatively where $X_2$=CHOH, this can be reduced to $CH_2$ for example using a reagent such as trimethylsilychloride and acetonitrile (Bull.Chem.Soc.Jpn., 1989, 62, 3537–3541).

Intermediates H can be prepared for example by reacting a commercially available ester F with an acid I in the presence of a strong acid such as a mixture of methanesulphonic acid and phophorous pentoxide (J. Med. Chem., 1995, 38, 1600–1607)

The preparation of I by standard methodology (from ethyl-3-bromo oxopentanoate and 4-(trifluoromethyl) thiobenzamide) is described below.

Alternatively (where n=2) H can be prepared from a commercially available ketone J, which is first protected as a benzyl derivative then reacted with an aldehyde to give unsaturated ketone K. Reduction followed by alkylation gives H (n=2)

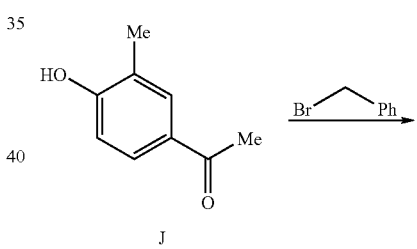

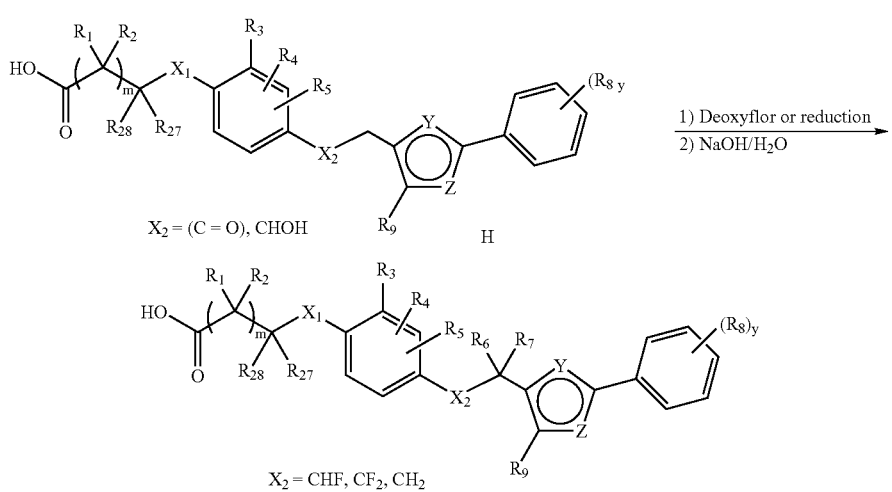

-continued

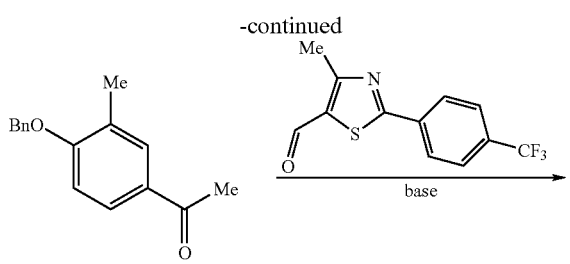

Synthesis of intermediates and Examples of the above schemes are shown in the Examples below. A person skilled in the art could apply analogous procedures to prepare compounds not specifically exemplified.

Those skilled in the art will recognize that stereocenters exist in compounds of formula (I). Accordingly, the present invention includes all possible stereoisomers and geometric isomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of formula (I) are possible, the present invention is intended to include all tautomeric forms of the compounds. In particular, in many of the preferred compounds of this invention the carbon atom to which $R^6$ and $R^7$ are bonded is chiral. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

The invention is further illustrated by the following Intermediates and Examples which should not be construed as constituting a limitation thereto.

Mass directed autoprep refers to methods where the material was purified by high performance liquid chromatography on a HPLCABZ+ 5 µm column (5 cm×10 mm i.d.) with 0.1% $HCO_2H$ in water and 95% MeCN, 5% water (0.5% $HCO_2H$) utilising gradient elution at a flow rate of 8 ml minutes$^{-1}$. The Gilson 202-fraction collector was triggered by a VG Plafform Mass Spectrometer on detecting the mass of interest.

Hydrophobic frit refers to filtration tubes sold by Whatman.

SPE (solid phase extraction) refers to the use of cartridges sold by International Sorbent Technology Ltd.

Intermediate 1

{4-methyl-2-[4-(trifluoromethyl)phenyl]-1,3-thiazol-5-yl}methanol

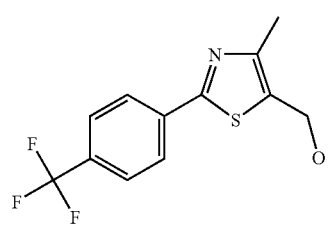

To a well stirred solution of lithium aluminium hydride (1.52 g) in dry tetrahydrofuran (50 ml) at 0° C., was slowly added a solution of ethyl 4-methyl-2-[4-(trifluoromethyl)phenyl]-thiazole-5-carboxylate (12.6 g) in dry tetrahydrofuran (50 ml). The mixture was stirred at room temperature for 2 hours. The reaction was quenched by slow addition at 0° C. of water (2 ml), 5N NaOH (2 ml) and water (6 ml). The precipitate was filtered, washed with ethyl acetate, methanol, dichloromethane and tetrahydrofuran. After evaporation, a yellow solid was obtained, that was crystallized from methanol-water to afford the title compound as a yellow solid.

mp 120–122° C.

Intermediate 2

4-methyl-2-[4-(trifluoromethyl)phenyl]-1,3-thiazole-5-carbaldehyde

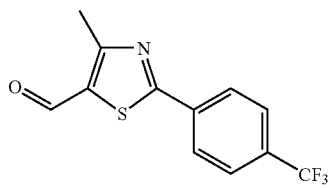

A mixture of {4-methyl-2-[4-(trifluoromethyl)phenyl]-1,3-thiazol-5-yl}methanol (intermediate 1, 2.52 g) in chloroform (200 ml) was treated with manganese dioxide (17.3 g) and the reaction mixture stirred for 2.5 hours. The reaction was filtered through Celite™ and the filtrate evaporated to give the title compound as a white solid.

$^1$H NMR (CDCl$_3$) δ 10.1 (s, 1H), 8.1 (d, 2H), 7.7 (d, 2H), 2.8 (s, 3H)

Intermediate 3

5-(bromomethyl)-4-methyl-2-[4-(trifluoromethyl)phenyl]-1,3-thiazole

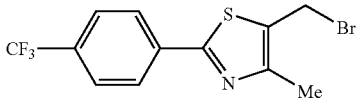

To a solution of {4-methyl-2-[4-(trifluoromethyl)phenyl]-1,3-thiazol-5-yl}methanol (intermediate 1, 0.9 g) in dry dichloromethane (30 ml) stirring at 0° C. was added carbon tetrabromide (1.1 g) and triphenylphosphine (0.995 g). The reaction was stirred at 0° C. for 1 hour, diluted with cyclohexane (30 ml) and purified by SPE cartridge (Si cartridge using chloroform:cyclohexane (1:1) to give the title compound as a white solid.

1H NMR (CDCl$_3$): δ 2.5 (s, 3H), 4.7 (s, 2H) 7.7 (d. 2H)

Intermediate 4 diethyl{4-methyl-2-[4-(trifluoromethyl)phenyl]-1,3-thiazol-5-yl}methylphosphonate

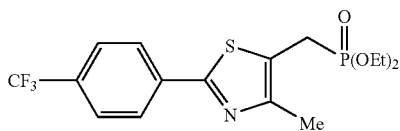

A mixture of 5-(bromomethyl)-4-methyl-2-[4-(trifluoromethyl)phenyl]-1,3-thiazole (intermediate 3, 1.48 g) and triethylphosphite (1.5 ml) was heated under nitrogen at 150° C. for 1 hour. The mixture was allowed to cool and excess triethylphosphite was removed under reduced pressure. This gave the title compound as a yellow solid.

HPLC Rt=3.51 minutes

Intermediate 5

4-Benzyloxy-3-methylbenzaldehyde

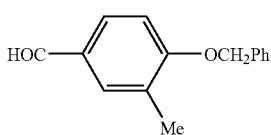

A mixture of 4-hydroxy-3-methylbenzaldehyde (0.658 g), benzyl bromide (0.812 g) and potassium carbonate (1.0 g) in acetone (30 ml) was stirred and heated under reflux for 6 hours. The solvent was removed and the residues were partitioned between water and ethyl acetate. The aqueous phase was further extracted with ethyl acetate and the combined organic layers were washed with brine and dried. Removal of the solvent gave the title compound as a brown oil.

HPLC Rt=3.81 minutes

Intermediate 6

5-{(E)-2-[4-(benzyloxy)-3-methylphenyl]ethenyl}-4-methyl-2-[4-(trifluoromethyl)phenyl]-1,3-thiazole)

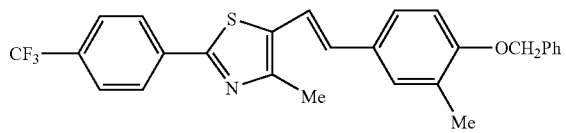

To a stirred solution of diethyl {4-methyl-2-[4-(trifluoromethyl)phenyl]-1,3-thiazol-5-yl}methylphosphonate (intermediate 4, 1.4 g) in dry tetrahydrofuran (10 ml) cooled in ice under nitrogen was added sodium hydride (0.12 g, 60% dispersion in mineral oil) and the reaction was stirred for 30 minutes. A solution of 4-benzyloxy-3-methylbenzaldehyde (0.724 g) in dry tetrahydrofuran (10 ml) was added dropwise, the reaction was allowed to come to room temperature and stirred for 2 hours. The solvent was removed and the residues partitioned between water (50 ml) and chloroform (50 ml). The aqueous phase was extracted with chloroform (20 ml) and the combined organics were washed with water and dried. Removal of solvent gave a solid which was purified by SPE chromatography. Elution with cyclohexane:ethyl acetate (20:1) gave the title compound as a yellow solid.

m/z (MH$^+$)=466

Intermediate 7

2-methyl-4-(2-{4-methyl-2-[4-(trifluoromethyl)phenyl]-1,3-thiazol-5-yl}ethyl)phenol

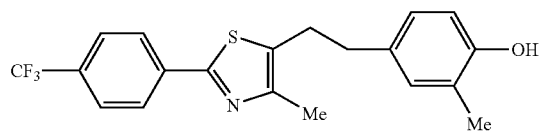

A solution of 5-{(E)-2-[4-(benzyloxy)-3-methylphenyl]ethenyl}-4-methyl-2-[4-(trifluoromethyl)phenyl]-1,3-thiazole)_(intermediate 6, 1.5 g) in glacial acetic acid (30 ml) was hydrogenated over 10% palladium on carbon (0.150 g). The catalyst was filtered off, the solvent was removed and the residues dissolved in ethyl acetate. This was washed with saturated sodium bicarbonate solution and brine. Drying and removal of solvent gave an oil which was purified by SPE (Si cartridge). Elution with cyclohexane:ethyl acetate gave the title compound as a white solid.

HPLC Rt=4.12 minutes

Intermediate 8

1-[4-(benzyloxy)-3-methylphenyl]ethanone

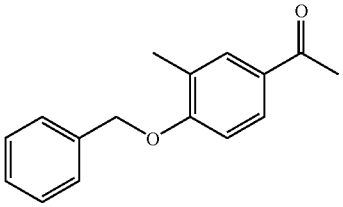

A mixture of 4-hydroxy-3-methylacetophenone (5.0 g) in dry acetonitrile (50 ml) was treated with potassium carbonate (5.06 g) and benzyl bromide (3.96 ml) and the reaction mixture heated at 40° C. After 3 hours the reaction was allowed to cool and was concentrated. The residue was partitioned between water and ethyl acetate; the aqueous layer separated and extracted twice more with ethyl acetate. The organic solutions were combined and were dried with brine and over magnesium sulfate and concentrated to give the title compound as a colourless oil HPLC Rt=3.65 minutes

Intermediate 9

2E)-1-[4-(benzyloxy)-3-methylphenyl]-3-{4-methyl-2-[4-(trifluoromethyl)phenyl]-1,3-thiazol-5-yl}prop-2-en-1-one

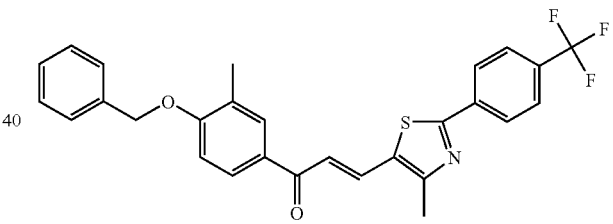

A mixture of 1-[4-(benzyloxy)-3-methylphenyl]ethanone (intermediate 8, 1.15 g) in dry tetrahydrofuran (15 ml) at −78° C. was treated dropwise with lithium diisopropylamide (2.6 ml of 2M solution in heptane/tetrahydrofuran/ethylbenzene) under nitrogen. The reaction mixture was warmed to 0° C. for 30 minutes. The mixture was cooled to −78° C. and 4-methyl-2-[4-(trifluoromethyl)phenyl]-1,3-thiazole-5-carbaldehyde (intermediate 2, 1.08 g) in dry tetrahydrofuran (15 ml) was added drop-wise at −78° C. and the reaction mixture stirred at 21° C. for 2 hours. Acetic acid (4 ml) in dry tetrahydrofuran (4 ml) was added followed by toluenesulphonic acid (0.1 g) and the reaction mixture was heated at 50° C. for 1 hour and then concentrated. The residue was partitioned between saturated bicarbonate solution and ethyl acetate; the aqueous layer separated and extracted thrice more with ethyl acetate. The organic solutions were combined and were dried with brine and over magnesium sulfate and concentrated. The product isolated after evaporation of the solvent was further purified by flash chromatography using cyclohexane:ethyl acetate (6:1) as eluent to give the title compound as a yellow solid.

HPLC Rt=4.70 minutes

Intermediate 10

1-(4-hydroxy-3-methylphenyl)-3-{4-methyl-2-[4-(trifluoromethyl)phenyl]-1,3-thiazol-5-yl}propan-1-one

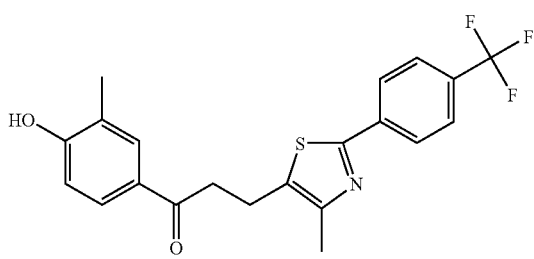

To a solution of (2E)-1-[4-(benzyloxy)-3-methylphenyl]-3-{4-methyl-2-[4-(trifluoromethyl)phenyl]-1,3-thiazol-5-yl}prop-2-en-1-one (intermediate 9, 0.77 g) in ethanol (30 ml) and 1,4-dioxane (10 ml) was added to 20% palladium hydroxide (0.31 g) and hydrogenated at 21° C. for 18 hours. The reaction was filtered through Celite and the filtrate evaporated to give material which was further purified by flash column chromatography using cyclohexane:ethyl acetate (3:1) as eluent to give the title compound as a colourless oil.

HPLC Rt=4.09 minutes

Intermediate 11 ethyl [2-methyl-4-(3-{4-methyl-2-[4-(trifluoromethyl)phenyl]-1,3-thiazol-5-yl}propanoyl)phenoxy]acetate

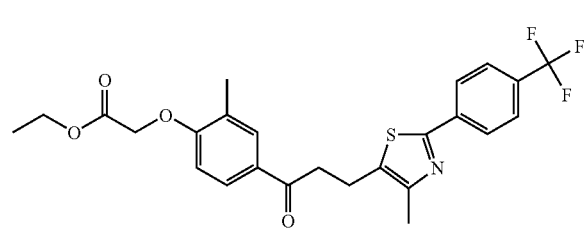

A solution of 1-(4-hydroxy-3-methylphenyl)-3-{4-methyl-2-[4-(trifluoromethyl)phenyl]-1,3-thiazol-5-yl}propan-1-one (intermediate 10, 0.28 g) in dry acetonitrile (15 ml) was treated with ethyl bromoacetate (0.076 ml) and cesium carbonate (0.449 g) and heated at 55° C. for 18 hours. The reaction was filtered, and the filtrate evaporated to give material which was further purified by flash column chromatography using cyclohexane:ethyl acetate (3:1) as eluent to give the title compound as a white solid.

HPLC Rt=4.18 minutes

Intermediate 12 ethyl [4-(1-hydroxy-3-{4-methyl-2-[4-(trifluoromethyl)phenyl]-1,3-thiazol-5-yl}propyl)-2-methylphenoxy]acetate

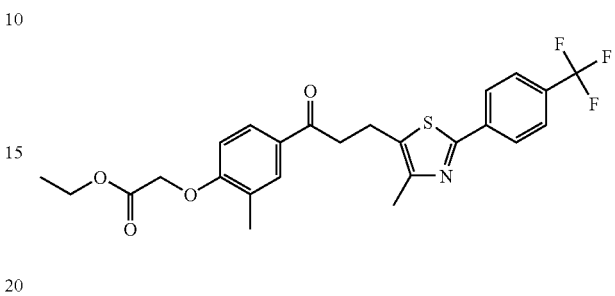

A mixture of ethyl [2-methyl-4-(3-{4-methyl-2-[4-(trifluoromethyl)phenyl]-1,3-thiazol-5-yl}propanoyl)phenoxy]acetate (intermediate11, 0.28 g) in tetrahydrofuran (8 ml) and water (8 ml) at 0° C. was treated portion-wise with sodium borohydride (0.043 g) and the mixture was stirred at 0° C. for 1 hour. The solvent was evaporated and the residue partitioned between water and ethyl acetate; the aqueous layer was separated and extracted twice more with ethyl acetate. The combined organic solutions were dried with brine and over magnesium sulfate and concentrated. The product isolated after evaporation of the solvent was further purified by flash column chromatography using cyclohexane:ethyl acetate (3:1) as eluent to give the title compound as a colourless gum.

HPLC Rt=4.03 minutes

Intermediate 13 ethyl {4-methyl-2-[4-(trifluoromethyl)phenyl]-1,3-thiazol-5-yl}acetate

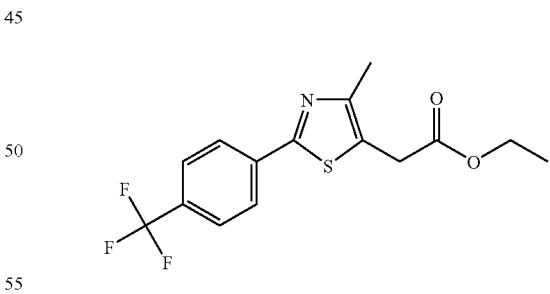

To a solution of ethyl-3-bromooxopentanoate (O. G. Kulinkovich e.t al., Synthesis, 1986, 378–379) (1.26 g) in absolute ethanol (6 ml) was added 4-(trifluoromethyl)thiobenzamide (1.24 g). The reaction was heated to reflux and stirred at this temperature for 18 hours under nitrogen. The mixture was then allowed to cool to room temperature, prior to cooling in ice. This resulted in crystallization of the product which was filtered and washed with ice cold ethanol to afford the title compound as beige crystals.

HPLC Rt=3.83 minutes

Intermediate 14

{4-methyl-2-[4-(trifluoromethyl)phenyl]-1,3-thiazol-5-yl}acetic acid

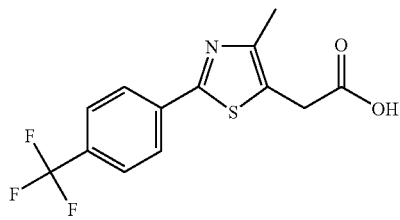

To ethyl{4-methyl-2-[4-(trifluoromethyl)phenyl]-1,3-thiazol-5-yl}acetate (intermediate 13, 0.5 g) in methanol (5 ml) was added 2M sodium hydroxide solution (3 ml). The resulting suspension was stirred at room temperature for 40 minutes, before the solvent was removed in vacuo. The residue was diluted with water (5 ml) acidified (2M hydrochloric acid) and the product extracted twice with ethyl acetate. The combined organic extracts were dried (magnesium sulfate), filtered and evaporated to give the title compound as a yellow solid.

HPLC Rt=3.55 minutes

Intermediate 15 ethyl [2-methyl-4-({4-methyl-2-[4-(trifluoromethyl)phenyl]-1,3-thiazol-5-yl}acetyl)phenoxy]acetate

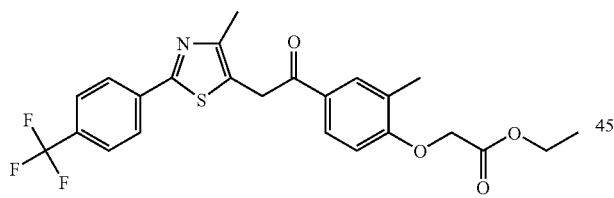

A well stirred suspension of phosphorus pentoxide (0.92 g) in methane sulfonic acid (6.5 ml) under nitrogen was heated to 60° C. until a clear solution formed. The mixture was then allowed to cool to room temperature prior to addition of {4-methyl-2-[4-(trifluoromethyl)phenyl]-1,3-thiazol-5-yl}acetic acid (intermediate 14, 0.98 g) and ethyl (2-methylphenoxy)acetate (0.49 ml). The mixture was heated to 60° C. for 90 minutes, after cooling to room temperature the reaction mixture was poured onto iced water (100 ml) and the acidic suspension basified by cautious addition of solid sodium bicarbonate. The product was extracted into ethyl acetate and the combined organic extracts dried (magnesium sulfate) filtered and evaporated. Purification by flash column chromatography using ethyl acetate:cyclohexane (1:9) as eluent gave title compound as a pale yellow solid.

HPLC Rt=4.12 minutes

Intermediate 16 ethyl [4-(1-hydroxy-2-{4-methyl-2-[4-(trifluoromethyl)phenyl]-1,3-thiazol-5-yl}ethyl)-2-methylphenoxy]acetate

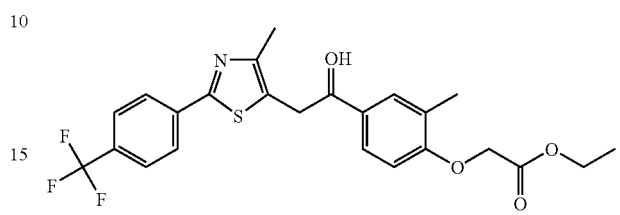

To a suspension of ethyl [2-methyl-4-({4-methyl-2-[4-(trifluoromethyl)phenyl]-1,3-thiazol-5-yl}acetyl)phenoxy]acetate (intermediated 15, 0.165 g) in absolute ethanol (5 ml) at 0° C. under nitrogen was added sodium borohydride (0.013 g) after stirring for an hour the reaction was allowed to come to room temperature and stirred for a further two hours. 2M aqueous hydrochloric acid was then added dropwise and once the effervescence had subsided water was added, the product was extracted twice with ethyl acetate and the combined organic extracts were dried (magnesium sulfate) filtered and evaporated. The product was purified by flash column chromatography using cyclohexane then ethyl acetate:cyclohexane(1:4) as eluents to give title compound as a pale yellow solid.

HPLC Rt=3.97 minutes

Intermediate 17 ethyl [4-(chloromethyl)-2-methylphenoxy]acetate

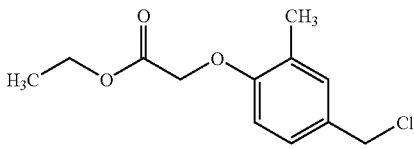

A mixture of ethyl (2-methylphenoxy)acetate (10.0 g) in petroleum ether (bp 40–60° C.) (24 ml) and concentrated hydrochloric acid (60 ml) was treated with 37% aqueous formaldehyde (4.2 ml) and the bi-phasic mixture stirred rapidly for 18 hours. The reaction mixture was diluted with ethyl acetate; the aqueous layer separated and the organic layer washed with water and then dried with brine and over sodium sulphate. The product isolated after evaporation of the solvent was further purified by flash title compound as a white solid m/z (M−Cl)$^+$ =207

Intermediate 18

4-(2-ethoxy-2-oxoethoxy)-3-methylbenzyl](triphenyl)phosphonium chloride

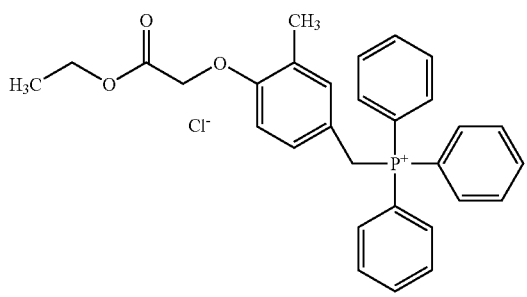

A mixture of [4-(2-ethoxy-2-oxoethoxy)-3-methylbenzyl](triphenyl)phosphonium chloride (intermediated 17, 2.5 g) and triphenylphosphine (2.73 g) in toluene (25 ml) was stirred at reflux for 68 hours. The reaction mixture was cooled and the title compound d, a white solid, isolated by filtration.

m/z (M–Cl)$^+$ =465

Intermediate 19 ethyl[2-methyl-4-(2-{4-methyl-2-[4-(trifluoromethyl)phenyl]-1,3-thiazol-5-yl}ethenyl)phenoxy]acetate

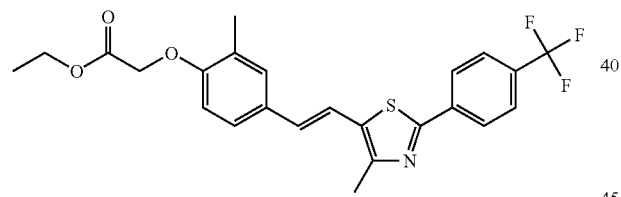

Sodium hydride (0.040 g, 60% dispersion in mineral oil) was added to anhydrous ethanol (20 ml) followed by [4-(2-ethoxy-2-oxoethoxy)-3-methylbenzyl](triphenyl)phosphonium chloride (intermediate 18, 0.45 g) after 10 minutes. After a further 10 minutes 4-methyl-2-[4-(trifluoromethyl)phenyl]-1,3-thiazole-5-carbaldehyde (intermediate 2, 0.24 g) was added and the reaction mixture stirred at ambient temperature for 3 hours. The reaction mixture was treated with water and then the mixture extracted with chloroform. The chloroform solution was separated with a hydrophobic frit and excess aldehyde removed using 3-[4-(hydrazinosulfonyl)phenyl]propionyl AM resin (0.50 g). The crude product remaining after this treatment was purified by Biotage™ chromatography using a mixture of petroleum ether:ethyl acetate (5:1) as eluent to give the title compound as a mixture of E and Z isomers.

m/z (MH)$^+$ =462

EXAMPLES

Example 1 ethyl [4-(1,1-difluoro-3-{4-methyl-2-[4-(trifluoromethyl)phenyl]-1,3-thiazol-5-yl}propyl)-2-methylphenoxy]acetate

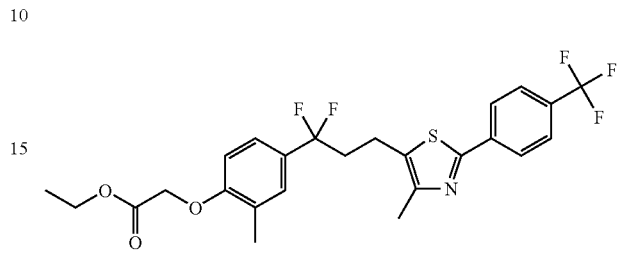

Ethyl [2-methyl-4-(3-{4-methyl-2-[4-(trifluoromethyl)phenyl]-1,3-thiazol-5-yl}propanoyl)phenoxy]acetate (intermediate 11, 0.15 g) was suspended in bis (2-methoxyethyl)aminosulfurtrifluoride (Deoxyfluor®)(2 ml) and heated at 85° C. for 72 hours. The reaction mixture was partitioned between saturated sodium bicarbonate solution and dichloromethane; the aqueous layer separated and extracted twice more with dichloromethane. The organic solutions were combined and were dried with brine and over magnesium sulfate and concentrated. The product isolated after evaporation of the solvent was further purified by flash column chromatography using cyclohexane:ethyl acetate (4:1) as eluent to give the title compound as colourless gum.

Example 2

[4-(1,1-difluoro-3-{4-methyl-2-[4-(trifluoromethyl)phenyl]-1,3-thiazol-5-yl}propyl)-2-methylphenoxy]acetic acid

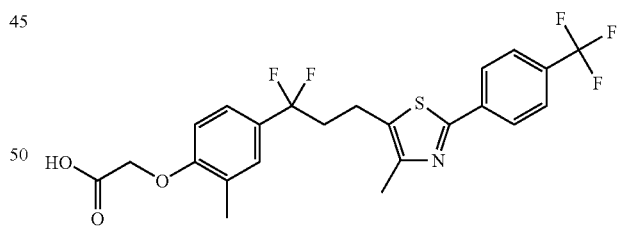

A mixture of ethyl [4-(1,1-difluoro-3-{4-methyl-2-[4-(trifluoromethyl)phenyl]-1,3-thiazol-5-yl}propyl)-2-methylphenoxy]acetate (example 1, 0.028 g) in tetrahydrofuran (4 ml) and 2M aqueous sodium hydroxide (4 ml) was stirred at 60° C. for 2 hours. The solvent was evaporated and the residue partitioned between ether and water; the aqueous layer was acidified using 10% w/v aqueous citric acid and then extracted thrice with ethyl acetate. The combined ethyl acetate solutions were dried over magnesium sulfate and evaporated to give the title compound.

m/z (M–H)$^-$ =484

HPLC Rt=4.18 minutes

Example 3 ethyl[2-methyl-4-(3-{4-methyl-2-[4-(trifluoromethyl)phenyl]-1,3-thiazol-5-yl}propyl)phenoxy]acetate

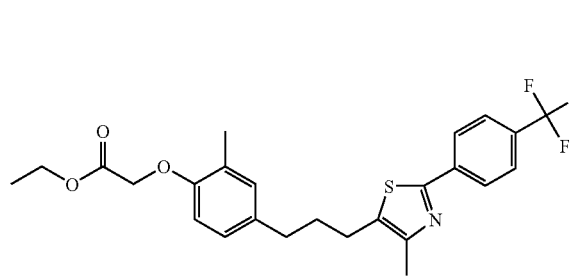

To a stirred mixture of trimethylsilylchloride (0.15 ml), sodium iodide (0.175 g) and acetonitrile (0.061 ml) was added a solution of ethyl [4-(1-hydroxy-3-{4-methyl-2-[4-(trifluoromethyl)phenyl]-1,3-thiazol-5-yl}propyl)-2-methylphenoxy]acetate (intermediate 12, 0.096 g) in cyclohexane (1 ml). The reaction mixture was stirred at 21° C. for 18 hours and then refluxed for 2 hours. The reaction mixture was partitioned between water and ethyl acetate; the aqueous layer separated and extracted twice more with ethyl acetate. The organic solutions were combined and were dried with brine and over magnesium sulfate and concentrated. The product isolated after evaporation of the solvent was further purified by flash chromatography using cyclohexane: ethyl acetate (7:1) as eluent to give the title compound as a pale yellow gum.

Example 4

[2-methyl-4-(3-{4-methyl-2-[4-(trifluoromethyl)phenyl]-1,3-thiazol-5-yl}propyl)phenoxy]acetic acid

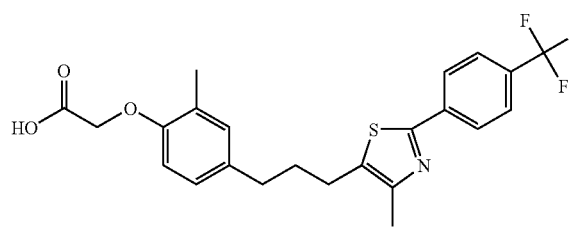

Prepared by hydrolysis of example 3 using an analogous procedure to that described for the preparation of example 2
HPLC Rt=4.97 minutes
m/z (M−H)⁻ 448

Example 5 ethyl [4-(1-fluoro-2-{4-methyl-2-[4-(trifluoromethyl)phenyl]-1,3-thiazol-5-yl}ethyl)-2-methylphenoxy]acetate

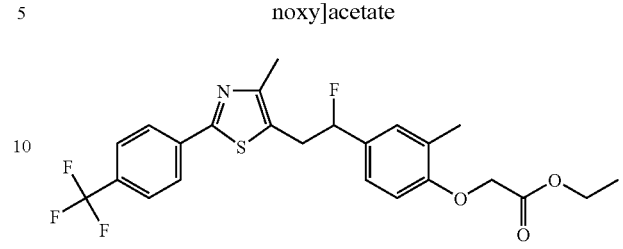

To a solution of bis-(2-methoxyethyl)aminosulfur trifluoride (0.031 g) in anhydrous dichloromethane (0.05 ml) at −78° C. under nitrogen was added a solution of ethyl [4-(1-hydroxy-2-{4-methyl-2-[4-(trifluoromethyl)phenyl]-1,3-thiazol-5-yl}ethyl)-2-methylphenoxy]acetate (intermediate 16, 0.061 g) in anhydrous dichloromethane (1 ml). After two hours at −78° C. the reaction was quenched with saturated sodium bicarbonate solution (2.5 ml) and the product extracted into dichloromethane. The organic extract was separated by hydrophobic frit and evaporated to yield a yellow oil. Purification by flash column chromatography using neat cyclohexane and ethyl acetate:cyclohexane (1:9) as eluents to give the title compound as a yellow solid.

Example 6

[4-(1-fluoro-2-{4-methyl-2-[4-(trifluoromethyl)phenyl]-1,3-thiazol-5-yl}ethyl)-2-methylphenoxy]acetic acid

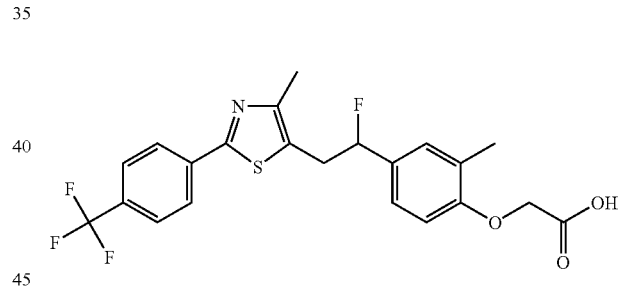

Prepared by hydrolysis of example 5.
HPLC Rt=4.19 minutes
m/z (MH⁺) 454

Examples 7 and 8 ethyl [2-methyl-4-(1,1,2-trifluoro-2-{4-methyl-2-[4-(trifluoromethyl)phenyl]-1,3-thiazol-5-yl}ethyl)phenoxy]acetate (example 7)

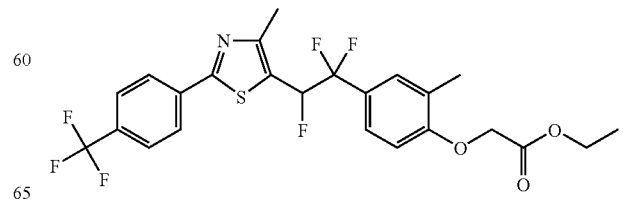

and:

ethyl [2-methyl-4-(1,1,2,2-tetrafluoro-2-{4-methyl-2-[4-(trifluoromethyl)phenyl]-1,3-thiazol-5-yl}ethyl)phenoxy]acetate (example 8)

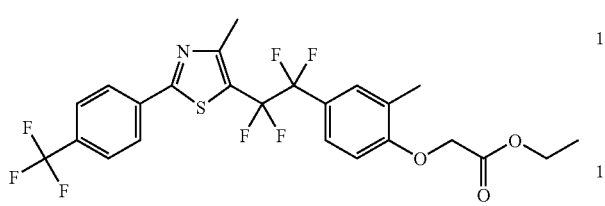

To ethyl [2-methyl-4-({4-methyl-2-[4-(trifluoromethyl)phenyl]-1,3-thiazol-5-yl}acetyl)phenoxy]acetate (intermediate 15, 0.155 g) was added bis-(2-methoxyethyl)amino sulfur trifluoride (1 ml). The mixture was then heated to 85° C. for 66 hours, after this time the reaction was allowed to cool to room temperature and then quenched by pouring into iced saturated sodium carbonate solution (50 ml), the products were extracted into dichloromethane. The combined organic extracts were dried (sodium sulfate) filtered and evaporated to yield the crude products. Purification by flash column chromatography using ethyl acetate:cyclohexane (1:9) as eluent gave the title compound (example 8) as a pale yellow oil.

HPLC Rt=4.50 minutes
m/z (MH$^+$) 536

Further elution with ethyl acetate:cyclohexane (1:9) gave the other title compound (example 7) as a pale yellow oil.

HPLC Rt=4.32 minutes
m/z (MH$^+$) 518

Example 9

[2-methyl-4-(1,1,2,2-tetrafluoro-2-{4-methyl-2-[4-(trifluoromethyl)phenyl]-1,3-thiazol-5-yl}ethyl)phenoxy]acetic acid

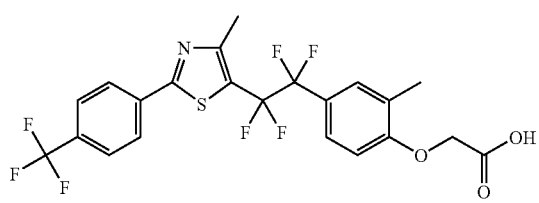

prepared by hydrolysis of example 8
HPLC Rt=4.55 minutes
m/z (MH)$^+$ 508

Example 10

[2-methyl-4-(1,1,2-trifluoro-2-{4-methyl-2-[4-(trifluoromethyl)phenyl]-1,3-thiazol-5-yl}ethyl)phenoxy]acetic acid

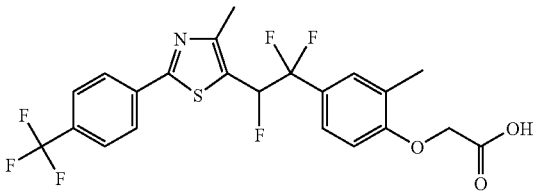

Prepared by hydrolysis of example 7
HPLC Rt=4.25 minutes,
m/z (MH)$^+$490

Example 11

Methyl 4-[2-methyl-4-(2-{4-methyl-2-[4-(trifluoromethyl)phenyl]-1,3-thiazol-5-yl}ethyl)phenoxy]butanoate

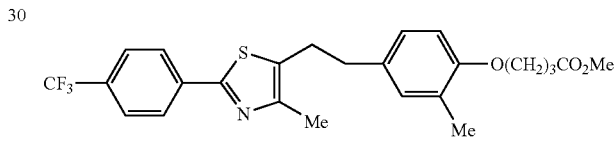

To a solution of 2-methyl-4-(2-{4-methyl-2-[4-(trifluoromethyl)phenyl]-1,3-thiazol-5-yl}ethyl)phenol (intermediate 7, 0.08 g) in acetonitrile (2 ml) was added methyl 4-bromobutyrate (0.090 g) and cesium carbonate (0.194 g). The mixture was stirred at room temperature for 24 hours then partitioned between water and ethyl acetate. The organic layer was dried, the solvent removed and the resulting oil was purified by SPE(Si cartridge). Elution with cyclohexane:ethyl acetate (20:1) gave the title compound as an oil which crystallised on standing.

HPLC Rt=4.48 minutes
m/z (MH)$^+$ 478

Example 12

4-[2-methyl-4-(2-{4-methyl-2-[4-(trifluoromethyl)phenyl]-1,3-thiazol-5-yl}ethyl)phenoxy]butanoic acid

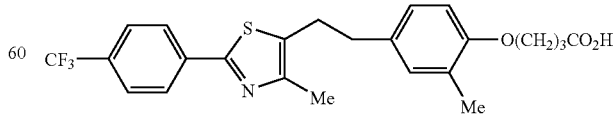

prepared by hydrolysis of example 11
HPLC Rt=4.32 minutes
m/z (M–H)$^-$ 462

Example 13

Methyl 5-[2-methyl-4-(2-{4-methyl-2-[4-(trifluoromethyl)phenyl]-1,3-thiazol-5-yl}ethyl)phenoxy]pentanoate

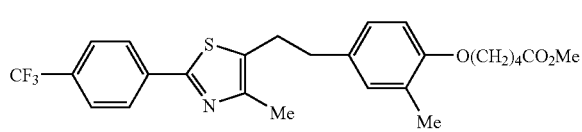

Prepared in an analogous manner to example 11 from intermediate 7 and methyl 5-bromopentanoate.

Example 14

5-[2-methyl-4-(2-{4-methyl-2-[4-(trifluoromethyl)phenyl]-1,3-thiazol-5-yl}ethyl)phenoxy]pentanoic acid

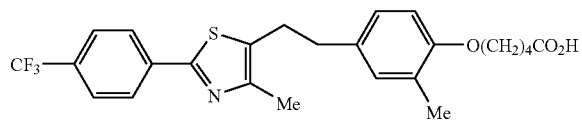

Prepared by hydrolysis of example 13
HPLC Rt=4.41 minutes
m/z (M–H)⁻ 476

Example 15 ethyl [2-methyl-4-(2-{4-methyl-2-[4-(trifluoromethyl)phenyl]-1,3-thiazol-5-yl}ethyl)phenoxy]acetate

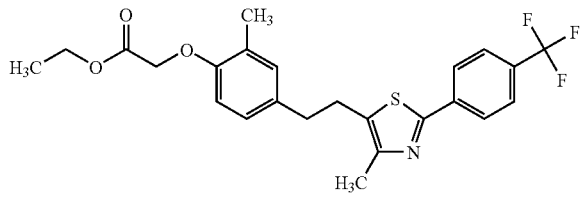

A mixture of ethyl [2-methyl-4-(2-{4-methyl-2-[4-(trifluoromethyl)phenyl]-1,3-thiazol-5-yl}ethenyl)phenoxy]acetate (intermediate 19, 0.23 g) and 10% palladium on carbon (0.2 g) in ethanol:1,4-dioxan (1:1, 20 ml) was stirred under a hydrogen atmosphere for 6 hours. The reaction mixture was filtered through Celite™ and the filtrate evaporated. The residue was purified by Biotage™ chromatography using a mixture of petroleum ether:ethyl acetate (4:1) as eluent to give the title compound as a pale yellow solid.

Example 16

[2-methyl-4-(2-{4-methyl-2-[4-(trifluoromethyl)phenyl]-1,3-thiazol-5-yl}ethyl)phenoxy]acetic acid

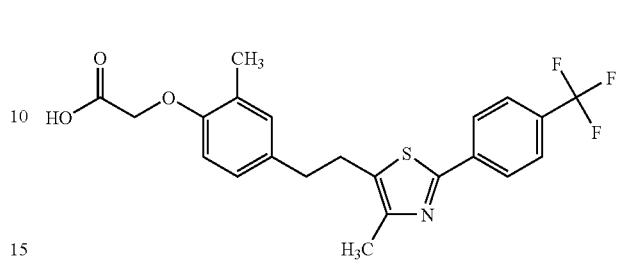

Prepared by hydrolysis of example 15
m/z (MH)⁺ =436
HPLC Rt=4.2 minutes
The following intermediates and ligands were prepared for the binding and transfection assays described below:

(i) 2-{2-methyl-4-[({4-methyl-2-[4-(trifluoromethyl)phenyl]-1,3-thiazol-5-yl}methyl)sulfanyl]phenoxy}acetic acid This compound was used as a PPARdelta reference in the transfection assays described below and was prepared according to the method reported in WO200100603-A1.

(ii) 2-methyl-2-[4-{[(4-methyl-2-[4-trifluoromethylphenyl]-thiazol-5-yl carbonyl)amino]methyl}-phenoxy] propionic acid This compound was used as a PPAR alpha reference in the transfection assay described below and was prepared according to method reported in WO200140207-A1.

(iii) 5-{4-[2-(Methyl-pyridin-2-yl-amino)-ethoxy]-benzyl}-thiazolidine-2,4-dione This compound (also referred to as rosiglitazone) was used as a PPAR gamma reference in the transfection assay described below and was prepared according to method reported in *J. Med. Chem.* 1994, 37(23), 3977.

Binding Assay

Compounds were tested for their ability to bind to hPPAR gamma hPPARalpha or PPARdelta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand (3H-BRL 49653 for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002)and labelled GW 2433 (see Brown, P. J et al. Chem. Biol. 1997, 4, 909–918. For the structure and synthesis of this ligand) for PPAR delta) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent KI values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. Anal. Biochem. 1998, 257, 112–119).

Transfection Assay

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), J. Biol. Chem., 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and beta-galactosidase activity. Alkaline phosphatase activity was corrected for transfection efficiency using the beta-galactosidase activity as an internal standard (see, for example, Kliewer, S. A., et. al. Cell 83, 813–819 (1995)). Rosiglitazone (BRL 49653) was used as a positive control in the hPPAR gamma assay. The positive control in the hPPAR alpha assays was 2-methyl-2-[4-{[(4-methyl-2-[4-trifluoromethylphenyl]-thiazol-5-yl-carbonyl)amino]methyl}-phenoxy]propionic acid. The positive control for PPAR delta assays was 2-{2-methyl-4-[({4-methyl-2-{trifluoromethyl)phenyl]-1,3-thiazol-5-yl}methyl)sulfanyl]phenoxy}acetic acid.

What is claimed is:

1. A compound of formula (I) or pharmaceutically acceptable salts and solvates thereof wherein

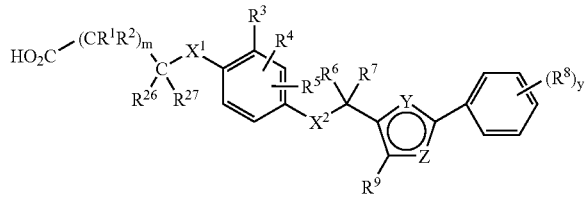

(IC)

$R^1$ and $R^2$ are independently H or C1–3alkyl;
m is 0–3;
$X^1$ is NH, NCH$_3$, O, or S;
$R^3$, $R^4$ and $R^5$ are independently H, CH$_3$, CF$_3$, OCH$_3$, allyl or halogen;
$X^2$ is $(CR^{10}R^{11})$n wherein n is 1 or 2;
$R^{10}$ and $R^{11}$ independently represent H, fluorine or $C_{1-6}$ alkyl;
$R^{26}$ and $R^{27}$ are independently H, $C_{1-3}$ alkyl or $R^{26}$ and $R^{27}$ together with the carbon atom to which they are bonded form a 3–5 membered cycloalkyl ring;
$R^6$ and $R^7$ independently represent H, fluorine or $C_{1-6}$ alkyl;
$R^9$ is $C_{1-6}$ alkyl or CF$_3$;
one of Y and Z is N, the other is S or O;
each $R^8$ independently represents CF$_3$, OCH$_3$, CH$_3$ or halogen; y is 0, 1, 2, 3, 4, 5.

2. A pharmaceutical composition comprising a compound of claim 1.

3. A pharmaceutical composition according to claim 2 further comprising a pharmaceutically acceptable diluent or carrier.

* * * * *

UNITED STATES PATENT AND TRADEMARK OFFICE
CERTIFICATE OF CORRECTION

PATENT NO. : 7,196,107 B2 Page 1 of 1
APPLICATION NO. : 10/451307
DATED : March 27, 2007
INVENTOR(S) : Beswick et al.

It is certified that error appears in the above-identified patent and that said Letters Patent is hereby corrected as shown below:

On the Title page:

Item (30) should read as follows:

(30)   Foreign Application Priority Data
   Dec. 20, 2000   (GB)   ........................0031109.2

Signed and Sealed this

Seventeenth Day of July, 2007

JON W. DUDAS
*Director of the United States Patent and Trademark Office*